United States Patent [19]

Haring et al.

[11] Patent Number: 5,246,718
[45] Date of Patent: Sep. 21, 1993

[54] STARCHES WITH AN IMPROVED FLAVOR

[75] Inventors: Petrus G. M. Haring, Vlaardingen; Petrus M. T. De Kok, Vlaardingen; Ronald P. Potman, Schiedam; Johannes J. Wesdorp, Roosendaal, all of Netherlands

[73] Assignee: Van den Bergh Foods Co., Division of Conopco, Inc., Lisle, Ill.

[21] Appl. No.: 833,270

[22] Filed: Feb. 10, 1992

[30] Foreign Application Priority Data

Feb. 11, 1991 [EP] European Pat. Off. ............ 91200282

[51] Int. Cl.$^5$ .......................................... A23L 1/0522
[52] U.S. Cl. ........................................ 426/18; 426/44; 426/578; 426/661; 426/48; 435/212; 435/219; 435/220; 435/275; 127/71
[58] Field of Search ............... 426/18, 44, 48, 578, 426/661; 435/212, 219, 220, 275; 127/71

[56] References Cited

U.S. PATENT DOCUMENTS

| | | | |
|---|---|---|---|
| 3,167,432 | 1/1965 | Colby | 426/18 |
| 3,364,034 | 1/1968 | Hoersch et al. | 426/18 |
| 3,488,256 | 1/1970 | High et al. | 435/275 |
| 4,282,319 | 8/1981 | Conrad | 426/18 |
| 4,303,451 | 12/1981 | Seidel et al. | 426/578 |
| 4,368,212 | 1/1983 | Hechman | 426/578 |
| 4,377,602 | 3/1983 | Conrad | 426/661 |
| 4,477,480 | 10/1984 | Seidel et al. | 426/578 |
| 4,551,335 | 11/1985 | Canella et al. | 426/44 |
| 4,847,371 | 7/1989 | Schara | 426/578 |
| 4,940,662 | 7/1990 | Yamazaki et al. | 435/272 |
| 5,139,809 | 8/1992 | Wienen et al. | 426/578 |

FOREIGN PATENT DOCUMENTS 0223560 5/1987 European Pat. Off. .
2406665 5/1979 France .

Primary Examiner—Jeanette Hunter
Attorney, Agent, or Firm—Gerard J. McGowan, Jr.

[57] ABSTRACT

The present invention relates to a method for improving the flavor of starch by incubating the starch with an enzymatically active peptidase containing cell preparation under such conditions that enzymatic peptidolysis of a substantial amount of oligopeptides in the starch is the result, which incubation is, optionally, preceded or followed by a non-enzymatic purification step such as steam stripping or solvent extraction. The starch is suited for incorporation into food products, such as spreads.

16 Claims, No Drawings

STARCHES WITH AN IMPROVED FLAVOR

The present invention is concerned with a method for improving the flavor of starches.

In Edible Starches and Starch-derived syrups, Noyes Data Corporation (1975), London, starch is said to be a high-polymeric carbohydrate of general formula $(C_6H_{10}O_5)_n$, where n varies from a few hundred to over one million (page 1). The term starch whenever referred to in this document, not only encompasses (native) starch according to the above definition, but also amylose and amylopectin, starch hydrolysates such as maltodextrins, gelatinized starches and chemically modified starches such as cross-linked starches, starch esters and starch ethers.

The above mentioned starches are incorporated in various food products for diverse purposes. Generally in such food applications, it is desirable that the starches employed have a bland flavor. Commercially available starches, however, usually do not possess a bland flavor. A bitter-like off-flavor may be noticed when tasting the starch as such, and sometimes, in a food composition, only after admixture with other food ingredients.

An enzymatic treatment of starch is known from East German patent 139 361. A method is provided for treating cereal starch containing insoluble gluten, wherein the gluten adhered to the starch is removed by treatment with a protease.

It has been found that this bitter-like off-flavor can be removed or at least reduced substantially by treating the starch with an enzymatically active cell preparation under such conditions that enzymatic peptidolysis of a substantial amount of oligopeptides in the starch is the result. The cell preparation may contain various types of enzymes, inter alia peptidases. According to the invention a method is provided for obtaining a starch with an improved flavor by having this starch incubated with said enzymatically active cell preparation.

A preferred embodiment is the use of the method for improving the flavor of a starch which is essentially gluten free and which contains a significant amount of oligopeptides.

The starch preferably is a gelling starch. More preferably said starch is selected from the group consisting of hydrolyzed starch, such as maltodextrins, and chemically modified starch and mixtures thereof. The present method is most preferably used to improve the flavor of hydrolyzed starches.

The starch may originate from tapioca, rice, corn, potato or other plants, but preferably originates from potato.

The term peptidase as used throughout this document encompasses exo-peptidases which releases from peptides the N-terminal or C-terminal amino acids or dipeptides (e.g. aminopeptidase, carboxypeptidase, dipeptidase, dipeptidyl peptidase).

According to a preferred embodiment of the present invention the cell preparations are obtained from food grade bacteria, preferably lactic acid bacteria, particularly *Lactococcus lactis* (formerly denoted as *Streptococcus lactis*).

The cell preparations may comprise intact cells, but, preferably, are obtained by lysing the cells, optionally followed by extracting the lysate. The crude cell lysate and the cell extract can be used without further purification.

According to another preferred embodiment of the present method a cell preparation having a relatively high peptidase activity is utilized. Accordingly the cell preparation preferably has a peptidase activity of at least 0.001 Units. More preferably the peptidase activity exceeds 0.01 Units. It should be noted that the present method is not restricted to the use of one single peptidase, but also includes the use of mixtures of peptidases.

The aminopeptidase activity can suitably be determined by a standard method described in European patent application EP-A-0 223 560 which is based on the hydrolysis of L-Leucine para-nitro-anilide and the ensuing release of para-nitro-aniline, which is determined.

Generally food grade starches contain only minute amounts, e.g. less than 0.5 wt % of oligopeptides. Typically the untreated starch used in the present method contains from 0.002–0.3 wt % of oligopeptides and particularly 0.005–0.1 wt %.

By oligopeptides, whenever referred to in this document, are meant peptides comprising from 3–30 amino acid groups. Polypeptides comprising more than 30 amino acid groups are referred to as proteins.

Preferably the enzymatic treatment of the starch material in accordance with the invention is carried out under such conditions that there is a substantial rise in the amount of free amino acids. Substantial rise is understood to be an increase of the amino acid concentration with a factor of at least 1.5, preferably at least 2. The starch according to the invention is therefore characterized by the presence of an amount of free amino acids which is relatively high as compared to the total content of amino acids, peptides and protein, which can be indicated by the so called TNBS-value and which can be determined by a method described in J. Agric. Food Chem. 27, 1256 (1979). Generally in the refined starch the ratio of the free amino acid concentration (in $\mu$g/liter mixture) to the TNBS-value (in meq. Gly/liter mixture) exceeds 6000. Preferably the latter ratio exceeds 7500, more preferably the ratio exceeds 9000.

Because some cell preparations may show a slight amylase activity, obviously, incubation is stopped before degradation of the starch has occurred to an undesired degree.

The enzymatically treated starch has a bland taste and does no longer impart a contribution to the flavor of the composition in which it is used.

According to the invention the enzymatic treatment is suitably effected in an aqueous system. Preferably the enzymatic treatment is effected with a cell preparation containing 0.05 to 200 Units of peptidase per gram of oligopeptides in an aqueous system containing 0.1 to 40 wt % starch. The incubation conditions should be adequate for the conversion of flavor compounds. Therefore incubation should be allowed to continue for a sufficiently long period. According to a preferred embodiment of the present method incubation is continued for 0.1–60 hours, preferably 1–10 hours, at a pH in the range of 4–10, preferably 5–7 and a temperature in the range of 10°–70° C., preferably 20°–50° C.

Further improvements in reducing the flavor of starches can be achieved if the starch is also subjected to a second refining treatment, comprising a physical purification step, such as recrystallisation of the dissolved starch, absorption, adsorption, extraction by liquid and gas stripping. The second refining treatment may precede or follow the enzymatic treatment.

It has appeared to be particularly advantageous to subject the starch to gas stripping, preferably steam stripping, either before but preferably after the enzymatic treatment. Steam is blown through an aqueous dispersion or solution of starch for 0.1-100 hours, preferably 0.5-10 hours. The temperature is suitably kept between 60°-120° C. The duration and the temperature of the steam destillation treatment should be chosen such that undesired further hydrolysis of the starch is prevented.

Alternatively the starch may be subjected to an extraction treatment using a suitable food grade solvent other than water. Before extraction the starch is preferably dissolved or dispersed in water. A suitable solvent is n-hexane. For extraction one can use apparatus which are usual in the art. Preferred extraction times are 0.1-4 hours. A suitable temperature for extraction is 20°-120° C., preferably 40°-70° C. A further alternative purification step is an adsorption or absorption treatment of the starch with suitable adsorption or absorption agents. Such agent, should be water insoluble. A suitable absorbens is bleaching earth or active coal. Active coal e.g. is added to the starch solution in an amount of 0.1-0.5 wt % of the starch and bleaching earth in an amount of 0.1-2 wt %. The suspension is stirred for a period of 0.1-3 hours at a temperature of 20°-80° C. Subsequently it is filtrated or centrifuged. Alternatively so called pertraction can be applied which comprises a system in which the starch and the adsorbent/absorbent are in two phases separated by a semi-permeable membrane through which the off-flavor causing substance(s) can pass while the starch and the adsorbent/absorbent are kept separated.

For applying the refining treatment according to the invention there is no need to isolate the starch between or after both treatments. The refining treatment may be applied to a starch solution or dispersion which may subsequently be used in a food manufacturing process. But preferably the refined starch is converted into a dry form.

Another aspect of the present invention is a flavorless starch obtainable by the method according to the present invention. In this patent application by a flavorless starch is meant a starch which gives no perceptible flavor contribution to water to which it is admixed up to a concentration of 10 wt % or even of 15 wt %. The improved flavor is particularly appreciated if it is incorporated in food products at a concentration level of at least 3 wt %. The treated starches can advantageously be incorporated in various food products, especially food products wherein such starches are employed at relatively high concentration levels, e.g. low fat spreads, creams, dressings etc. Therefore a very preferred embodiment of the invention is an edible product containing the starch according to the invention. The product is e.g. a spread containing 0-60 wt % of fat phase and at least 40 wt % of aqueous phase, which contains starch at concentration levels of at least 1.5 wt % and even over 8% by weight of the aqueous phase.

Yet another aspect of the present invention is an enzymatically treated flavorless starch. The starch according to the invention is characterized by the presence of an amount of free amino acids which is relatively high as compared to the total content of amino acids, peptides and protein, which can be indicated by the TNBS-value mentioned before.

The invention is illustrated by means of the following examples:

EXAMPLE 1

Paselli SA2 TM, an enzymatically converted potato starch (ex. AVEBE, the Netherlands), containing max. 0.1 wt % protein on dry matter, was dissolved into tap water at a concentration level of 5 wt %. The starch solution so obtained was pasteurized at 85° C. for half an hour and after that the pH was adjusted to 7.0. Two batches A and B of 3 l. were taken from the starch solution. To batch B 0.01 wt % Corolase 7093 TM (a refined Aspergillus lysate ex ROEHM, Germany; activity=0.169 Units) was added, after which the batch was kept for 12 hours at 40° C. followed by pasteurization. Batch A was incubated with 0.01 wt % Debitrase TM (a lactic acid bacteria lysate ex IMPERIAL BIOTECHNOLOGY, UK; activity=0.197 Units) at a temperature of 37° C. for 6 hours and also pasteurized.

The batches A and B were used in the preparation of two batches of very low fat spread A' and B' and compared with a batch C' of a spread of identical formulation, but containing non-treated starch. The product formulation used was as follows:

|  | wt. % |
| --- | --- |
| Fat phase | |
| Fat blend | 26.65 |
| Monoglycerides (Dimodan OT TM) | 0.50 |
| Lecithin (Bolec ZTD TM) | 0.20 |
| Beta carotene (0.4%) | 0.15 |
| Aqueous phase | |
| Starch | 9.00 |
| Gelatin | 2.50 |
| Salt | 1.00 |
| Potassium sorbate | 0.12 |
| pH to 5.0 with 1% HCl | |
| Water to 100% | |

The very low fat spreads were produced at a throughput of 3.5 kg/hr from a premix of the aqueous and fat phase on a production line comprising a sequence of apparatus consisting of an A-unit (scraped surface heat exchanger), a C-unit (crystallizer), another A-unit and another C-unit. The processing conditions applied were as follows:

| Unit | Rotation Speed (r.p.m.) | Temp ex unit (°C.) |
| --- | --- | --- |
| A-unit | 800 | 10 |
| C-unit | 1500 | 22 |
| A-unit | 800 | 13 |
| C-unit | 250 | 17 |

The taste of the three batches very low fat spreads A', B' and C' so obtained was evaluated by an expert panel. It was established that the bitter-like off-flavor in the batches A' and B' has been reduced substantially compared to batch C'.

| | Organoleptic assay |
| --- | --- |
| Spread | Presence of bitter-like off-flavour |
| A' | −/+ |
| B' | −/+ |
| C' | + |

−: no off-flavour perceptible
−/+: faint perception of off-flavour
+: off-flavour clearly perceived An amino acid analysis was done for the untreated starch material (batch C) as well as the starch material that had been treated with Corolase ™ (batch B) and Debitrase ™ (batch A).

The following data were obtained (concentrations in μg/l of 15 wt % aqueous starch solution):

| Free Amino acid | Batch C | Batch A | Batch B |
|---|---|---|---|
| Asp | 28 | 174 | 130 |
| Thr | 8 | <5 | 514 |
| Ser | <5 | 93 | 361 |
| Glu | 48 | 149 | 183 |
| Pro | 31 | <5 | 53 |
| Gly | 16 | 110 | 188 |
| Ala | 5 | 138 | 649 |
| Cys | 30 | 30 | <5 |
| Val | 7 | 123 | 376 |
| Met | 39 | 18 | <5 |
| Ile | <5 | 80 | 182 |
| Leu | 25 | 193 | 322 |
| Tyr | 40 | 27 | 16 |
| Phe | 72 | 25 | 292 |
| Trp | 36 | 32 | 30 |
| Lys | 13 | 18 | 50 |
| Arg | 25 | <5 | 22 |
| Total | 423 | 1210 | 3368 |

The sample preparation for the above analysis included adding an equal amount of a trichloroacetic acid solution (24 wt % in water) to the starch solution and, centrifuging the mixture obtained, and analyzing the filtrate using the Waters amino acid analysis method with post-column derivatisation, employing o-phthalaldehyde as fluorescence probe.

In addition to the above analysis, the so called TNBS (TriNitroBenzeneSulfonic acid) method was used to determine the content of free amino groups in the sample-solutions. The samples were diluted by a factor 5 with a phosphate buffer (0.01M; pH=8; sodium dodecyl sulphate 0.6 g/l), so that a free amino-group concentration was obtained in the order of $1.10^{-2}$ g/l In an auto-analyzer the solutions were mixed with the TNBS-solution (3 g/l) and a phosphate reaction buffer (0.1M; sodium dodecyl sulphate 0.6 g/l; sodium sulphite 0.4 g/l; pH=8). The color of the yellow compound formed was measured using a spectrophotometer at 427 nm.

With the help of a calibration curve obtained for known glycine concentrations the amount of free N-terminal residues in the reaction mixture was calculated. The results obtained are represented below.

| Sample | TNBS-value* |
|---|---|
| Batch A | 0.12 |
| Batch B | 0.16 |
| Batch C | 0.10 |

*TNBS-values are given as meq. Gly/liter mixture

When the total free amino acid content (in μg/liter mixture) was divided by the TNBS-value, the following figures were obtained:

| Sample | Ratio total free amino acid/TNBS |
|---|---|
| Batch A | 10080 |
| Batch B | 21050 |
| Batch C | 4230 |

EXAMPLE 2

Paselli SA2 ™ was dissolved into tap water at a concentration level of 15 wt %. The starch solution so obtained was treated as follows:

A: Heated to 100° C. in an open vessel and injected with steam for 1 hour.

B: Pasteurized in a closed vessel at 85° C. for half an hour, cooled to 40° C. and incubated with 0.01 wt % Debitrase ™ at a temperature of 40° C. for 6 hours. Subsequently the suspension was heated to 100° C. in an open vessel and injected with steam for 1 hour.

C: Pasteurized in a closed vessel at 85° C. for half an hour.

After treatment the suspensions were stored at 5° C. 15 wt % aqueous starch slurries were prepared of each batch and at ambient temperature tested in an organoleptic assay:

| Batch | Organoleptic assay Presence of bitter-like off-flavour |
|---|---|
| A | +/− |
| B | − |
| C | ++ |

−: no off-flavour perceptible
−/+: faint perception of off-flavour
+: off-flavour clearly perceived
++: strong off-flavour The batches A, B and C were used in the preparation of very low fat spreads. With each batch two product were made, with (marked *) or without flavor (A'*, A', B'*, B', C'*, C'). The product formulation was as follows:

| Ingredient | wt. % | wt. % |
|---|---|---|
| Gelatin | 2.7 | 2.7 |
| Paselli SA2 ™ | 9.0 | 9.0 |
| Sodium chloride | 0.9 | 0.9 |
| Potassium sorbate | 0.09 | 0.09 |
| Beta-carotene | 0.00126 | 0.00126 |
| Calvetta palm-mid-fraction | 10.0 | 10.0 |
| Sodium caseinate | 0.335 | 0.335 |
| Flavour | — | 100 ppm |
| Lactic acid to pH 4.8 | | |
| The balance of water | | |
| pH | 4.80 | 4.80 |

All ingredients were mixed together and heated to 80° C. while stirring. The mixture was then cooled to 65° C. and homogenized at 3000 psi. The mixture was then cooled down by passage through a series of 2 A-units and collected.

| Spread | Organoleptic assay Presence of bitter-like off-flavour |
|---|---|
| A'* | +/− |
| B'* | − |
| C'* | ++ |
| A' | +/− |
| B' | − |
| C' | ++ |

−: no off-flavour perceptible
−/+: faint perception of off-flavour
+: off-flavour clearly perceived
++: strong off-flavour

We claim:

1. A method for improving the flavor of an essentially gluten-free starch comprising incubating the starch with an enzymatically active peptidase-containing cell preparation under such conditions that enzymatic peptidolysis of a substantial amount of oligopeptides in the starch is the result, said starch containing from 0.002-0.3 wt % of oligopeptides before bringing it into contact with the cell preparation, said method further comprising at least one physical purification step preceding or following said enzymatic treatment selected from the group consisting of recrystallization, absorption, adsorption, stripping by gas and extraction by liquid.

2. Method according to claim 1, wherein the starch is a hydrolyzed starch.

3. Method according to claim 1, wherein the cell preparation is derived from a lactic acid bacterium.

4. Method according to claim 1, wherein the cell preparation is derived from *Lactococcus lactis*.

5. Method according to claim 1, wherein the cell preparation has a peptidase activity of at least 0.001 Unit.

6. Method according to claim 1, which yields a starch wherein the ratio of the free amino acid concentration (in $\mu g/l$) to the TNBS-value (in meq.Gly/l) exceeds 6000.

7. Method according to claim 1, wherein the enzymatic treatment is effected with a cell preparation containing 0.05-200 Units peptidase per gram oligopeptides, in an aqueous system containing 0.1-40 wt % starch.

8. Method according to claim 1, wherein the enzymatic treatment is permitted to take place for 0.1-60 hours, at a pH in the range of 4-10 and a temperature in the range of 10°-70° C.

9. Method according to claim 8, wherein the enzymatic treatment is permitted to take place for 1-10 hours, at a pH in the range of 5-7 and a temperature in the range of 20°-50° C.

10. Method according to claim 1, wherein the physical purification step is steam stripping.

11. Method according to claim 10, wherein the starch solution or dispersion is contacted with steam during 0.1-100 hours at a temperature in the range 60°-120° C.

12. Flavorless starch, obtainable by the method according to claim 1.

13. Flavorless starch according to claim 12, wherein the ratio of the free amino acid concentration (in $\mu g/l$) to the TNBS-value (in meq. Gly/l) exceeds 6000.

14. Flavorless starch according to claim 12 which originates from potatoes.

15. Edible product containing a flavorless starch according to claim 12.

16. Edible dispersion comprising 0-60 wt % of fat phase and at least 40 wt % of aqueous phase which contains at least 1.5 wt % of a flavorless starch according to claims 12.

* * * * *